US012606641B2

(12) United States Patent
Mellor

(10) Patent No.: US 12,606,641 B2
(45) Date of Patent: Apr. 21, 2026

(54) AMPHIPHILIC CARBOHYDRATE COMPOUNDS

(71) Applicant: NANOMERICS LTD, St Albans (GB)

(72) Inventor: Ryan Mellor, London (GB)

(73) Assignee: NANOMERICS LTD, St Albans (GB)

( * ) Notice: Subject to any disclaimer, the term of this patent is extended or adjusted under 35 U.S.C. 154(b) by 625 days.

(21) Appl. No.: 17/926,772

(22) PCT Filed: May 21, 2021

(86) PCT No.: PCT/GB2021/051246

§ 371 (c)(1),
(2) Date: Nov. 21, 2022

(87) PCT Pub. No.: WO2021/234413

PCT Pub. Date: Nov. 25, 2021

(65) Prior Publication Data

US 2023/0220123 A1 Jul. 13, 2023

(30) Foreign Application Priority Data

May 22, 2020 (GB) ..................................... 2007703

(51) Int. Cl.

*C08B 37/08* (2006.01)
*A61K 31/436* (2006.01)
*A61K 31/722* (2006.01)
*A61K 38/13* (2006.01)

(52) U.S. Cl.

CPC .......... *C08B 37/003* (2013.01); *A61K 31/436* (2013.01); *A61K 31/722* (2013.01); *A61K 38/13* (2013.01)

(58) Field of Classification Search

CPC .. C08B 37/003; A61K 31/436; A61K 31/722; A61K 38/13
USPC .......................................................... 514/56
See application file for complete search history.

(56) References Cited

U.S. PATENT DOCUMENTS

2011/0206617 A1 8/2011 Roy et al.
2013/0203647 A1 8/2013 Uchegbu et al.

FOREIGN PATENT DOCUMENTS

| | | | |
|---|---|---|---|
| CN | 101058612 | A | 1/2010 |
| JP | 2004250543 | A | 9/2004 |
| WO | 2004026912 | A1 | 4/2004 |
| WO | 2008017839 | A1 | 2/2008 |
| WO | 2009152691 | A1 | 12/2009 |
| WO | 2010100479 | A1 | 9/2010 |
| WO | 2013109732 | A2 | 7/2013 |
| WO | 2015063510 | A1 | 5/2015 |
| WO | 2016071677 | A1 | 5/2016 |

OTHER PUBLICATIONS

Siew et al. Enhanced Oral Absorption of Hydrophobic and Hydrophilic Drugs Using Quaternary Ammonium Palmitoyl Glycol Chitosan Nanoparticles. Mol. Pharmaceutics 2012, 9, 14-28. (Year: 2012).*
Kale et al. Effect of fasting duration on clinical pathology results in Wistar rats. Vet Clin Pathol 38/3 (2009) 361-366. (Year: 2009).*
Chooi, K. W. et al. "Claw amphiphiles with a dendrimer core: Nanoparticle stability and drug encapsulation are directly proportional to the number of digits", Langmuir, 29, 13, 4214-4224 (2013).
Notice of Reason(s) for Rejection mailed on Feb. 25, 2025, in Japanese Patent Application No. 2022-571101.
International Search Report and Written Opinion issued on Aug. 11, 2021 in PCT/GB2021/051246.
International Preliminary Report on Patentability issued on Dec. 1, 2022 in PCT/GB2021/051246.
Qu et al. "Carbohydrate-Based Micelle Clusters Which Enhance Hydrophobic Drug Bioavailability by Up to 1 Order of Magnitude." Biomacromolecules, 7, 3452-3459. 2006.
Le et al. "Polymer Hydrophobicity Has a Positive Effect on the Oral Absorption of Cyclosporine A from Poly (ethylenimine) Based Nanomedicines." Pharmaceutical Nanotechnology, 1, 15-25. 2013.
Lu et al. "Preparation of water-soluble chitosan." Journal of Applied Polymer Science, 91, (6), 3497-3503. 2004.
Cho et al. "Preparation and solubility in acid and water of partially deacetylated chitins." Biomacromolecules, 1, (4), 609-14. 2000.
Hirano et al. "Water-Soluble N-(n-Fatty acyl) chitosans." Macromolecular Bioscience, 3, (10), 629-631. 2003.
Sogias et al. "Exploring the Factors Affecting the Solubility of Chitosan in Water." Macromolecular Chemistry and Physics, 211, (4), 426-433. 2010.
Park et al. "Synthesis and characterization of sugar-bearing chitosan derivatives: aqueous solubility and biodegradability." Biomacromolecules, 4, (4), 1087-91. 2003.
Cho et al. "Bioinspired tuning of glycol chitosan for 3D cell culture." NPG Asia Materials, 8, (9), e309-e309. 2016.
Godfrey et al. "Nanoparticulate peptide delivery exclusively to the brain produces tolerance free analgesia", J. Control Release, 270, 135-144. 2017.
Uchegbu et al. "Gene Transfer with Three Amphiphilic Glycol Chitosans—the Degree of Polymerisation is the Main Controller of Transfection Efficiency." Journal of Drug Targeting, vol. 12, No. 8, 1. Sep. 2004.
Uchegbu et al. "Chitosan amphiphiles provide new drug delivery opportunities." Polymer International, vol. 63, 7, 6. Mar. 2014.

(Continued)

*Primary Examiner* — Yih-Horng Shiao
(74) *Attorney, Agent, or Firm* — Meunier Carlin & Curfman LLC

(57) ABSTRACT

The present invention relates to an acetylated amphiphilic carbohydrate compound of average molecular weight 1-50 kDa which is based on a glycol chitosan, wherein the levels of acetylation can be modified. The compound can be formulated with hydrophobic compounds such as drugs. The degree of acetylation of the carbohydrate compound is optimised to maximise solubilisation of the drugs. The compound is formulated with drugs and is useful in therapy.

19 Claims, 2 Drawing Sheets

(56) References Cited

OTHER PUBLICATIONS

Office Action mailed on Jul. 2, 2025, in Chinese Application No. 202180060224.X.
Search Report mailed on Jun. 30, 2025, in Chinese Application No. 202180060224.X.
Decision to Refuse mailed on Jul. 8, 2025, in Japanese Application No. 2022-571101.
Odunze et al. "Unusual Enthalpy Driven Self Assembly at Room Temperature with Chitosan Amphiphiles," Pharmaceutical Nanotechnology, 7, 57-71 (2019).
Wu et al. "Radiation Technology and Advanced Materials," Shanghai Jiao Tong University Press, pp. 162-163 (Mar. 31, 2016).

* cited by examiner

AMPHIPHILIC CARBOHYDRATE COMPOUNDS

FIELD OF THE INVENTION

The present invention relates to acetylated amphiphilic carbohydrate compounds and their formulation with hydrophobic drugs.

BACKGROUND OF THE INVENTION

Amphiphilic carbohydrate compounds are useful for formulating drugs, particularly hydrophobic drugs. WO2004/026912 discloses carbohydrate polymers with hydrophobic and hydrophilic pendant groups suitable for solubilising, for example, compounds with hydrophobic character. The carbohydrate polymers may have the following general formula:

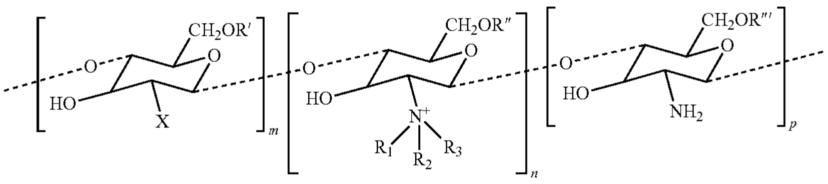

In this formula, X can be any linear or branched, substituted or unsubstituted or cyclo form of an alkyl, alkenyl, aryl, amine, amide, alcohol or acyl group. Preferably, the group X is a fatty acid derivative of, for example, palmitic acid. Smaller groups, such as acetamide, are not specifically disclosed. The value of m is from 0.01% to 10.00%.

Various studies have been carried out on the acetylation of chitosan and its derivatives. The influence of acetylation on chitosan amphiphile derivatives' self-assembly and drug encapsulation, has not been studied extensively however. The acetyl group on chitosan is hydrophobic and therefore one might expect that the higher the degree of acetylation, the more hydrophobic the acetylated chitosan would become. A more hydrophobic (higher level of acetylation) chitosan amphiphile would be expected to self assemble more readily and encapsulate higher levels of hydrophobic compounds, as hydrophobicity promotes self assembly and drug encapsulation (Qu et al., "Carbohydrate-based micelle clusters which enhance hydrophobic drug bioavailability by up to 1 order of magnitude", Biomacromolecules 2006, 7, 3452-3459). Increasing hydrophobicity of other polymers also increases their ability to self assemble and both encapsulate and deliver hydrophobic compounds via the oral route (Le et al., "Polymer hydrophobicity has a positive effect on the oral absorption of cyclosporine A from poly(ethylenimine) based nanomedicines", Pharmaceutical Nanotechnology, 2013, 1, 15-25.) However, the relationship between hydrophobicity (as measured by aqueous solubility), and the level of acetylation of chitosan is complex. As such it is not possible to predict that a level of acetylation on a chitosan amphiphile will have a positive effect on the encapsulation efficiency of hydrophobic drugs.

Based on the above, it is important to appreciate the relationship between the acetyl derivatisation of chitosan and the hydrophobicity (reduced water solubility) of the resulting chitosan derivatives if one wishes to prepare amphiphilic and self-assembling chitosan derivatives for use as pharmaceutical or other product excipients.

The water solubility of chitosan increases with increasing levels of deacetylation (~34% to ~64%) and at about half deacetylation (~50% acetyl groups) chitosan is water soluble, due to the reduced crystallinity offered by the acetyl groups (Lu et al., "Preparation of water-soluble chitosan", *Journal of Applied Polymer Science* 2004, 91, (6), 3497-3503 and Cho et al. "Preparation and solubility in acid and water of partially deacetylated chitins", *Biomacromolecules* 2000, 1, (4), 609-14). Further studies have shown that N-acetyl chitosans with an acetylation level of between 42-82% are water soluble (Hirano et al., "Water-Soluble N-(n-Fatty acyl) chitosans.", *Macromolecular Bioscience* 2003, 3, (10), 629-631).

Other studies have shown that chitosan (0.5% w/w) also becomes more soluble in dilute acetic acid as the level of deacetylation increases from 9-55% (Cho et al. "Preparation and solubility in acid and water of partially deacetylated chitins", *Biomacromolecules* 2000, 1, (4), 609-14). There is thus literature evidence to suggest that at 50% acetylation chitosan is at its most water soluble (Lu et al., "Preparation of water-soluble chitosan", *Journal of Applied Polymer Science* 2004, 91, (6), 3497-3503) and that chitosan's hydrophobicity increases as the level of deacetylation decreases below 50%. However, the influence of deacetylation on the water solubility of chitosan when the levels of deacetylation are above 70% are not clear and there are no clear trends. For example, in the case of chitosans with a level of acetylation of 14%, 50% or no detectable acetylation (fully deacetylated), fully deacetylated chitosan starts to precipitate at pH=5.8, 14% acetylated chitosan starts to precipitate at pH=6.0 and 50% acetylated chitosan starts to precipitate at pH=7.4; all studied at 1 mg/ml (Sogias et al., "Exploring the Factors Affecting the Solubility of Chitosan in Water", *Macromolecular Chemistry and Physics* 2010, 211, (4), 426-433). This suggests that at neutral pH (pH=7.0), fully deacetylated chitosan and 14% acetylated chitosan are insoluble, whereas half deacetylated chitosan is soluble. Additionally 72% deacetylated chitosan, is reported to be insoluble in water (Lu et al., "Preparation of water-soluble chitosan", *Journal of Applied Polymer Science* 2004, 91, (6), 3497-3503). When chitosans are additionally derivatised the relationship between the level of acetylation and the water solubility of chitosan is no clearer. Acetylated sugar bearing chitosans (2 mg/mL) with sugar levels of 5% are insoluble in water when acetylation levels range from 5 to 29% and at an acetylation level of 68%, but a sugar-bearing chitosan with a sugar level of 5% and acetylation level of 49% is water soluble (Park et al. "Synthesis and characterization of sugar-bearing chitosan derivatives: aqueous solubility and biodegradability", *Biomacromolecules* 2003, 4, (4), 1087-91).

Additionally, N-acetyl-glycol chitosans with an acetylation range of 73-92% have been shown to be water soluble (Cho et al., "Bioinspired tuning of glycol chitosan for 3D cell culture." *NPG Asia Materials* 2016, 8, (9), e309-e309).

As is apparent from the above, there is an absence of clear direction in the existing literature as to where the optimum level of acetylation resides to prepare hydrophobic chitosan amphiphile derivatives with a good ability to encapsulate hydrophobic compounds. The present invention is based on studies on the effect of acetylation on the self-assembly and, in turn, drug encapsulation of amphiphilic chitosan derivatives. Optimised amphiphilic carbohydrate compounds for encapsulating hydrophobic drugs are provided.

SUMMARY OF THE INVENTION

In a first aspect, the present invention provides an amphiphilic carbohydrate compound of average molecular weight 1-50 kDa of the following formula (I):

(I)

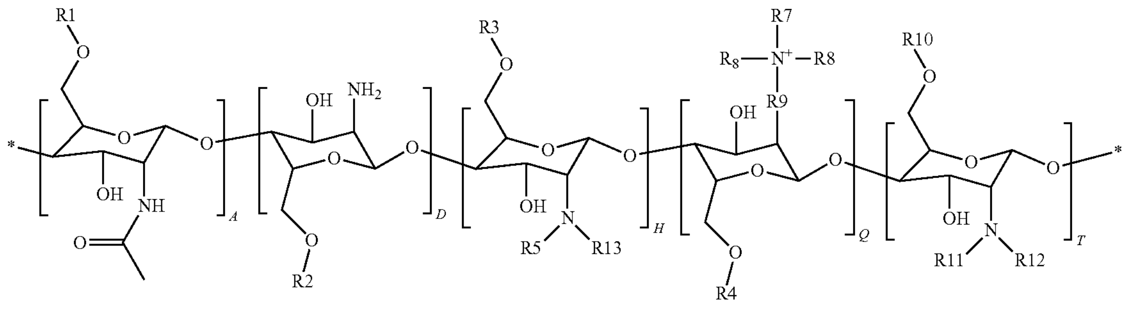

wherein:

the level of unit A is from 0.5% to 30 mole % the level of unit D is from 1% to 95.5 mole %;

the level of unit H is from 1% to 95.5 mole %;

the level of unit Q is from 3% to 97.5 mole %;

the level of unit T is from 0% to 94.5 mole %;

$R^1$, $R^2$, $R^3$, $R^4$ and $R^{10}$ are independently hydrogen or any linear, branched or cyclo form of an alkyl, alkenyl, alkynyl, aryl, acyl group, a sugar substituent selected from glucose, galactose, fructose, and muramic acid, or oligo polyoxa $C_1$-$C_3$ alkylene units, optionally substituted with amine, amide or alcohol;

$R^5$ is a hydrophobic, substituted or unsubstituted, linear, branched or cyclo form of a $C_{4-30}$ alkyl, $C_{4-30}$ alkenyl, $C_{4-30}$ alkynyl, $C_{4-30}$ aryl, amine, $C_{4-30}$ amide, $C_{4-30}$ alcohol or $C_{3-30}$ acyl group;

$R^6$, $R^7$, and $R^8$ are independently any linear, branched, or cyclo forms of any alkyl, alkenyl, alkynyl, aryl or acyl group;

$R^9$ may be present or absent and, when present, is a substituted or unsubstituted alkyl group, a substituted or unsubstituted amine group or a substituted or unsubstituted amide group;

$R^{11}$ is a substituted or unsubstituted alkyl group, a substituted or unsubstituted ether group or a substituted or unsubstituted alkene group or hydrogen; and $R^{12}$ is a substituted or unsubstituted alkyl group, a substituted or unsubstituted ether group or a substituted or unsubstituted alkene group;

$R^{13}$ is a substituted or unsubstituted alkyl group, a substituted or unsubstituted ether group or a substituted or unsubstituted alkene group or hydrogen;

or a salt thereof.

In accordance with a second aspect of the invention there is provided a pharmaceutical composition comprising an amphiphilic carbohydrate compound according to the first aspect of the invention, a hydrophobic drug, and one or more pharmaceutically acceptable excipients.

In accordance with a third aspect of the invention there is provided a composition comprising an amphiphilic carbohydrate compound according to the first aspect of the invention and a hydrophobic drug, for use in therapy.

In accordance with a fourth aspect of the invention there is provided a method of forming an amphiphilic carbohydrate compound according to the first aspect of the present invention, wherein the method comprises depolymerisation of a carbohydrate compound;

increasing, decreasing or maintaining the level of acetylation;

reacting the carbohydrate with a compound to add a hydrophobic side chain; and reacting the carbohydrate with a compound to produce a quaternary ammonium group.

Also provided is an agrochemical composition comprising an amphiphilic carbohydrate compound according to the first aspect of the invention, an agrochemical agent and one or more agrochemically acceptable excipients.

Also provided a method of controlling fungal contamination with an agrochemical composition according to the fifth aspect of the invention.

It would be expected that increasing the degree of acetylation of an amphiphilic carbohydrate compound such as quaternary ammonium palmitoyl glycol chitosan (GCPQ) would allow for stronger hydrophobic interactions with hydrophobic molecules and therefore greater encapsulation of a hydrophobic drug. The present inventors, however, surprisingly observed the opposite effect. The present invention reveals that controlling the degree of acetylation (the level of unit A in the formula above) in combination with an appropriate degree of hydrophobicity (unit H in the formula above) is an effective way to increase the solubilisation of hydrophobic compounds.

DETAILED DESCRIPTION OF INVENTION

Figure 1:
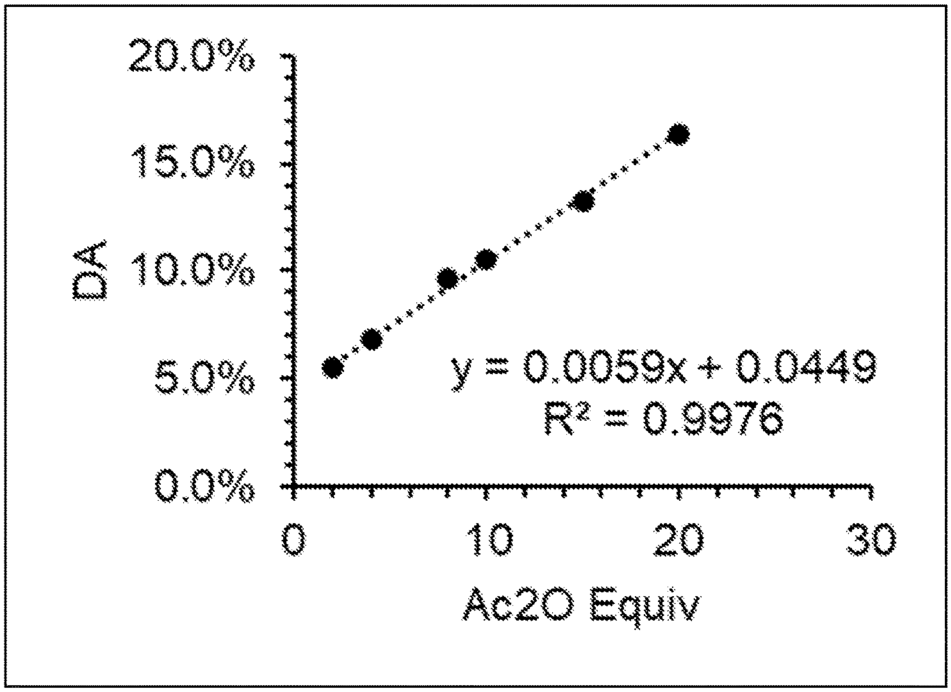
FIG. 1 shows the levels of acetylation (DA) obtained with various equivalents of acetic anhydride.
Figure 2:
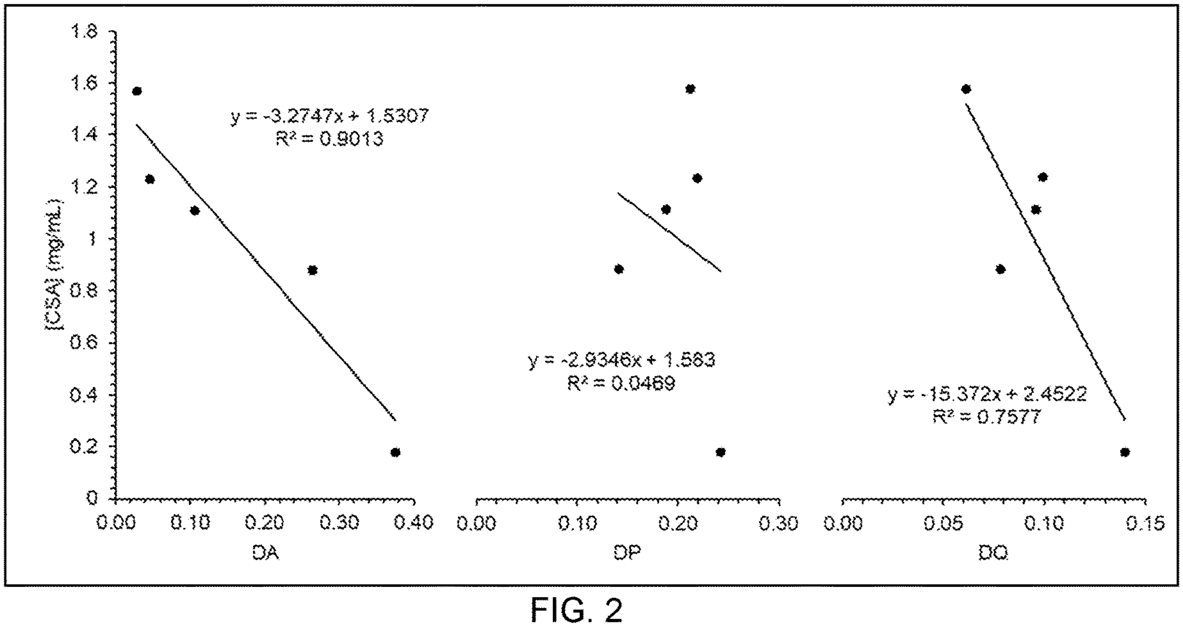
FIG. 2 shows the levels of cyclosporine A solubilisation as a function of the level of acetylation, the level of palmitoylation and the level of quaternisation respectively.
Figure 3:
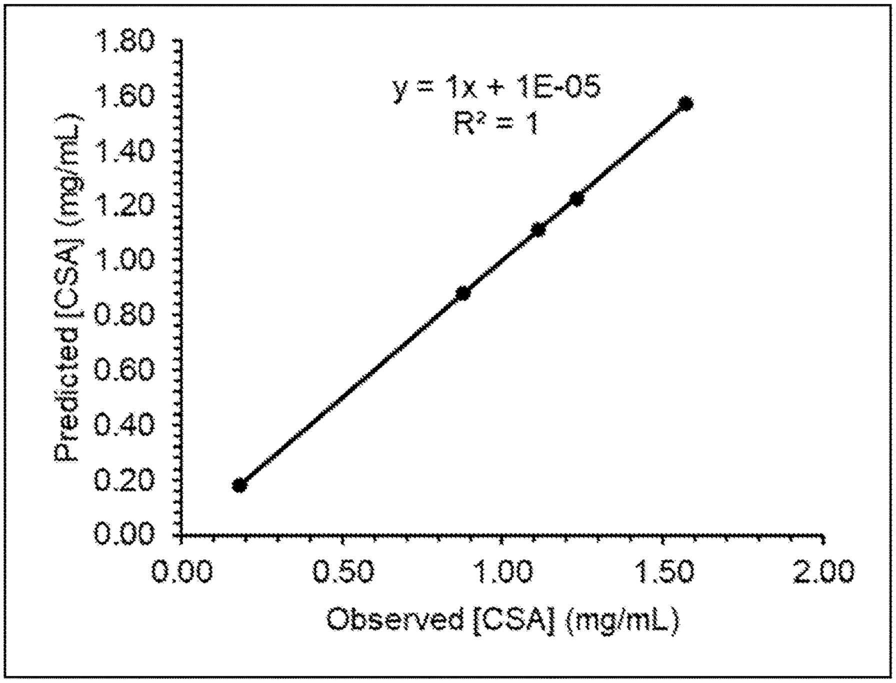
FIG. 3 shows the observed levels of cyclosporine A solubilisation against those predicted by mathematical modelling.
Figure 4:
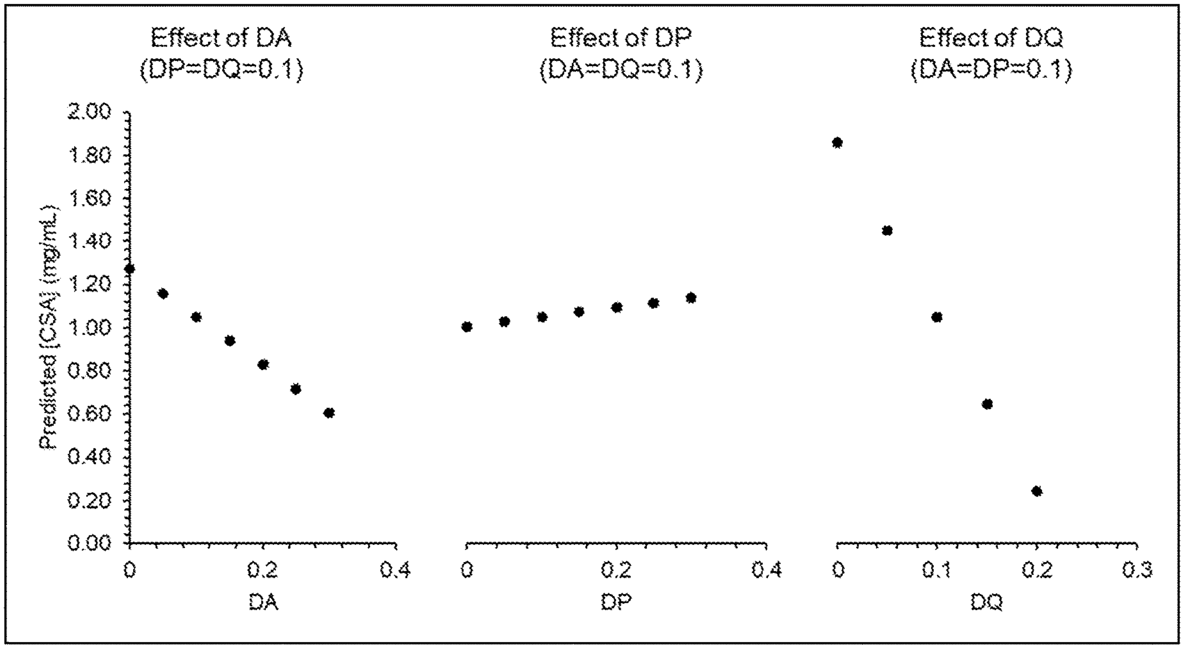
FIG. 4 shows the predicted levels of cyclosporine A solubilisation as a function of the level of acetylation, the level of palmitoylation and the level of quaternisation respectively in theoretical polymers.

As detailed above, the present invention describes an amphiphilic carbohydrate compound of average molecular weight 1-50 kDa according to the formula (I), or a salt thereof, which is reproduced again below for ease of reference:

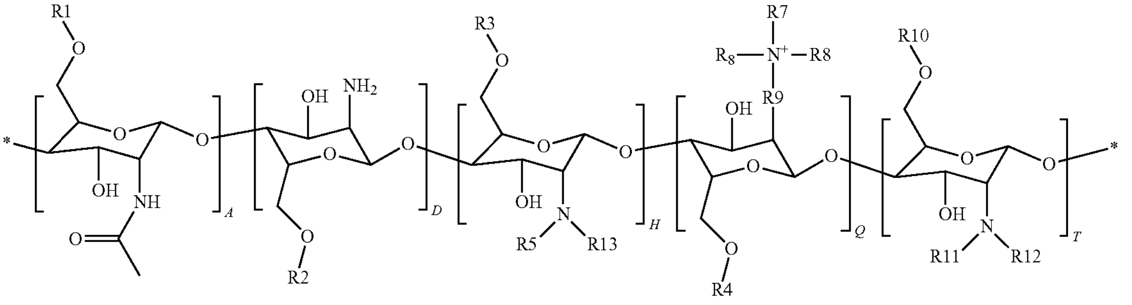

(I)

In this formula:

* is used to represent the continuing polymer chain;

the level of unit A (the acetylated unit) is from 0.5% to 30 mole % the level of unit D (the deacetylated unit) is from 1% to 95.5 mole %;

the level of unit H (the hydrophobized unit) is from 1% to 95.5 mole %;

the level of unit Q (the quaternary amine unit) is from 3% to 97.5 mole %;

the level of unit T (the tertiary amine unit) is from 0% to 94.5 mole %.

All percentages refer to mole %.

It is understood that A+D+H+Q+T will be equal to 100%. It should also be understood that A, D, H, Q and T may form any arrangement in the amphiphilic carbohydrate compound. The arrangement may therefore be entirely random or as a block copolymer form such as ADHQADHQ etc.

The present invention provides a method for maximising compound solubilisation by means of a varying acetylation level of a polymer.

In one preferred embodiment of the invention, unit T is absent. The following preferred ranges apply whether unit T is present, or not.

In a preferred embodiment of the invention, A is in the range 0.5% to 26 mole %, preferably in the range 0.5% to 20 mole %, preferably in the range 0.5% to 15 mole %, more preferably in the range 0.5% to 10 mole %, even more preferably in the range 0.5% to 5 mole % or 0.5 to 4 mole % or 0.5 to 3 mole %.

In an alternative preferred embodiment, A is in the range 2 to 20 mole %, preferably 2 to 15 mole %, more preferably in the range 2 to 10 mole %, even more preferably in the range 2 to 5 mole % or 2 to 4 mole %.

In an alternative preferred embodiment, A is in the range 1 to 20 mole %, preferably 1 to 15 mole %, more preferably in the range 1 to 10 mole %, even more preferably in the range 1 to 5 mole % or 2 to 5 mole %.

In a preferred embodiment of the invention, D is in the range 2% to 94.5 mole %, preferably in the range 10% to 94.5 mole %, more preferably in the range 10% to 90 mole %, typically in the range 20 to 80 mole % or 50% to 75 mole %, more preferably in the range 55% to 75 mole %, even more preferably in the range 65% to 75 mole %.

In a preferred embodiment of the invention, H is in the range 2% to 94.5 mole %, preferably in the range 2% to 90 mole %, more preferably in the range 5% to 80 mole %. In a further preferred embodiment, H is in the range 5% to 70 mole %, for instance 5% to 60 mole % or 5% to 50 mole %.

In an alternative embodiment, H is in the range 10% to 30 mole %, more preferably in the range 10 to 20 mole % or 20% to 30 mole %.

In a preferred embodiment of the invention, Q is in the range 1% to 90 mole %. It is preferably present in the range 2% to 50 mole %, for instance 5% to 30 mole %, 5% to 20 mole %, 5 to 15 mole % or 5 to 10 mole %.

In a preferred embodiment of the invention, T is in the range 0% to 20 mole %, more preferably in the range 0% to 10 mole %, even more preferably in the range 0% to 5 mole %. In some embodiments, T is present in the range 0.5% to 20 mole % or 1% to 20 mole %, for instance, 1 to 10 mole % or 1 to 5 mole %.

Any of the preferred ranges for A, D, H, Q and T may be combined.

In a preferred embodiment the following ranges are present:

A is in the range 2 to 30 mole %;

H is in the range 14 to 24 mole %;

Q is in the range 6 to 14 mole %.

In a further preferred embodiment, the following ranges are present:

A is in the range 2 to 11 mole %;

H is in the range 10 to 24 mole %;

Q is in the range 6 to 14 mole %.

The amphiphilic carbohydrate may be accompanied by a salt. For instance, the salt can comprise a chloride, iodide, acetate or glucuronide salt.

The molecular weight of the amphiphilic carbohydrate compound has a molecular weight in the range 1-50 kDa. Molecular weight is preferably measured using Gel-permeation chromatography-multi-angle light scattering (GPC-MALLS).

The amphiphilic carbohydrate compound is capable of self-assembly into nanoparticles in aqueous media.

$R^1$, $R^2$, $R^3$, $R^4$ and $R^{10}$ are independently hydrogen or any linear, branched or cyclo form of an alkyl, alkenyl, alkynyl, aryl, acyl group, a sugar substituent selected from glucose, galactose, fructose, and muramic acid, or oligo polyoxa $C_1$-$C_3$ alkylene units, optionally substituted with amine, amide or alcohol. Preferably these groups are independently selected from hydrogen, a substituted or unsubstituted alkyl group, a substituted or unsubstituted ether group, or a substituted or unsubstituted alkene group.

Typically, $R^1$, $R^2$, $R^3$, $R^4$ and $R^{10}$ may be $C_1$-$C_4$ linear alkyl groups. Conveniently, $R^1$, $R^2$, $R^3$, $R^4$ and $R^{10}$ may all be —$CH_2$—$CH_2$—OH.

Typically, $R^1$, $R^2$, $R^3$, $R^4$ and $R^{10}$ may be $C_1$-$C_4$ linear glycol-based groups.

Typically, $R^1$, $R^2$, $R^3$, $R^4$ and $R^{10}$ are any of the following sugar substituents: glucose, galactose, fructose, and muramic acid.

$R^1$, $R^2$, $R^3$, $R^4$ and $R^{10}$ may be oligo polyoxa $C_1$-$C_3$ alkylene units such as ethylene glycol oligomers.

All of $R^1$, $R^2$, $R^3$, $R^4$ and $R^{10}$ may be $CH_2OCH_2CH_2OH$ or $CH_2CH_2OH$.

All of $R^1$, $R^2$, $R^3$, $R^4$ and $R^{10}$ may be H.

Typically, $R^5$ is a hydrophobic, substituted or unsubstituted, linear, branched or cyclo form of a $C_{4-30}$ alkyl, $C_{4-30}$ alkenyl, $C_{4-30}$ alkynyl, $C_{4-30}$ aryl, amine, $C_{4-30}$ amide, $C_{4-30}$ alcohol or $C_{3-30}$ acyl group.

The group $R^5$ is preferably selected from a substituted or unsubstituted group which is an alkyl group such as a $C_{4-30}$ alkyl group, an alkenyl group such as a $C_{4-30}$ alkenyl group, an alkynyl group such as a $C_{4-30}$ alkynyl group, an aryl group such as a $C_{5-20}$ aryl group, a multicyclic hydrophobic group with more than one $C_4$-$C_8$ ring structure such as a sterol (e.g. cholesterol), a multicyclic hydrophobic group with more than one $C_4$-$C_8$ heteroatom ring structure, a polyoxa $C_1$-$C_4$ alkylene group such as polyoxa butylene polymer, or a hydrophobic polymeric substituent such as a poly (lactic acid) group, a poly (lactide-co-glycolide) group or a poly (glycolic acid) group. The $R^5$ group may be linear, branched or cyclo groups.

Preferred examples of $R^5$ groups include those represented by the formulae $CH_3(CH_2)_n$—CO— or $CH_3(CH_2)_n$— or the alkeneoic acid $CH_3(CH_2)_p$—CH═CH—$(CH_2)_q$—CO—, where n is between 4 and 30, and more preferably between 6 and 20, and p and q may be the same or different and are between 4 and 16, and more preferably 4 and 14. A particularly preferred class of $R^5$ substituents are linked to the chitosan monomer unit via an amide group (including the pendant NH in the formula), for example as represented by the formula $CH_3(CH_2)_nCO$—, where n is between 2 and 28. Examples of amide groups are produced by the coupling of carboxylic acids to the amine group of chitosan. Preferred examples are fatty acid derivatives $CH_3(CH_2)_nCOOH$ such as those based on capric acid (n=8), lauric acid (n=10), myristic acid (n=12), palmitic acid (n=14), stearic acid (n=16) or arachidic acid (n=18).

$R^6$, $R^7$, and $R^8$ are independently any linear, branched, or cyclo forms of any alkyl, alkenyl, alkynyl, aryl or acyl group. $R^6$, $R^7$ and $R^8$ are preferably independently selected from a substituted or unsubstituted alkyl group such as a $C_{1-10}$ alkyl group. $R^6$, $R^7$ and/or $R^8$ may be linear or branched. Preferably, $R^6$, $R^7$ and $R^8$ are independently selected from methyl, ethyl or propyl groups.

Conveniently, $R^6$, $R^7$ and $R^8$ form a quaternary ammonium group which is hydrophilic.

Hydrophilic groups are groups which are well hydrated by water and associate on a molecular level with water. A further non-ionic hydrophilic group may replace $NR^6R^7R^8$ providing that $R^6$, $R^7$ and $R^8$ are equal to $CH_2O$—Y where Y is a hydrophilic substituent. In that case both hydrophilic substituents on the carbohydrate polymer may be selected from mono and oligo hydroxy $C_1$-$C_6$ alkyl, mono and oligo hydroxy substituted $C_2$-$C_6$ acyl, $C_1$-$C_2$ alkoxy alkyl optionally having one or more of the hydroxy groups substituted on the alkoxy or alkylene groups, oligo or poly-(oxa $C_1$-$C_2$ alkylene), preferably polyethylene glycol comprising up to 120 ethylene oxide units (i.e. a molecular weight of 5000), and $C_1$-$C_4$ alkyl (oligo or poly oxa $C_1$-$C_3$ alkylene) optionally hydroxy substituted preferably oligo or polyglycerol ether; wherein the replacement group for $NR^6R^7R^8$ is joined via an ether linkage to a saccharide unit of the polysaccharide. The acyl group may contain alkyl, alkenyl or alkynyl groups.

$R^1$, $R^2$, $R^3$, $R^4$ and $R^{10}$ may also be hydrophilic.

The $R^9$ group may be present or absent in the general formula. $R^9$ may be present or absent and, when present, is a substituted or unsubstituted alkyl group, a substituted or unsubstituted amine group or a substituted or unsubstituted amide group;

When absent, it provides a quaternary ammonium functional group that is directly linked to the monomer unit of the chitosan backbone. When the $R^9$ group is present it may be a unsubstituted or substituted alkyl group (e.g. a $C_{1-10}$ alkyl group) for example as represented by —$(CH_2)_n$— wherein n is preferably 1 to 4. A preferred example of the $R^9N^+R^6R^7R^8$ substituent is provided by coupling betaine (—OOC—$CH_2$—$N^+$—$(CH_3)_3$) to the amine substituent of the b unit providing an amide group such as in: —NH—CO—$CH_2$—$N^+R^6R^7R^8$.

$R^{11}$ is a substituted or unsubstituted alkyl group, a substituted or unsubstituted ether group or a substituted or unsubstituted alkene group or hydrogen. Preferably $R^{11}$ is selected from hydrogen and a substituted or unsubstituted alkyl group such as a $C_{1-10}$ alkyl group. $R^{11}$ may be linear or branched. Preferably, $R^{11}$ is selected from methyl, ethyl or propyl groups. Alternatively, it is an OH-substituted alkyl group, preferably of formula $CH_2CH_2OH$.

$R^{12}$ is a substituted or unsubstituted alkyl group, a substituted or unsubstituted ether group or a substituted or unsubstituted alkene group. Preferably $R^{12}$ is selected from substituted or unsubstituted alkyl group such as a $C_{1-10}$ alkyl group. $R^{12}$ may be linear or branched. Preferably, $R^{12}$ is selected from methyl, ethyl or propyl groups. Alternatively, it is an OH-substituted alkyl group, preferably of formula $CH_2CH_2OH$.

Typically, $R^{12}$ is a $C_{1-10}$ alkyl group. $R^{12}$ may be linear or branched. Preferably, $R^{12}$ is selected from methyl, ethyl or propyl groups.

$R^{13}$ is a substituted or unsubstituted alkyl group, a substituted or unsubstituted ether group or a substituted or unsubstituted alkene group or hydrogen. Preferably $R^{13}$ is selected from hydrogen and a substituted or unsubstituted alkyl group such as a $C_{1-10}$ alkyl group. $R^{13}$ may be linear or branched. Preferably, $R^{13}$ is selected from methyl, ethyl or propyl groups. Alternatively, it is an OH-substituted alkyl group, preferably of formula $CH_2CH_2OH$. Most preferably $R^{13}$ is hydrogen.

The total number of monomer units of A+D+H+Q+T may be about 10 to 100. Preferably the total number of monomer units of A+D+H+Q+T may be less than about 200.

The amphiphilic carbohydrate compound may also contain additional targeting groups such as peptides, antibodies and other ligands, for example, folate and transferrin ligands which may allow the polymer to target endogenous receptors and thus target its drug payload to such endogenous receptors at the site of pathology.

In a preferred embodiment of the invention, the amphiphilic carbohydrate compound is a partially deacetylated form of N-palmitoyl, N-monomethyl, N, N-dimethyl, N,N, N-trimethyl-6-O-glycolchitosan (GCPQ). This is known to be an amorphous compound (Godfrey et al., "Nanoparticulate peptide delivery exclusively to the brain produces tolerance free analgesia", *J. Control Release* 2017, 270, 135-144) and so is not bound by the increase in crystallinity observed when acetylated chitosan is converted to deacetylated chitosan.

As indicated, some of the substituents described herein may be either unsubstituted or substituted with one or more additional substituents as is well known to those skilled in the art. Examples of common substituents include halo; hydroxyl; ether (e.g., $C_{1-7}$ alkoxy); formyl; acyl (e.g. $C_{1-7}$ alkylacyl, $C_{5-20}$ arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$ alkylthio); sulphonic acid; sulfonate; sulphone; sulfonyloxy; sulfinyloxy; sulfamino; sulfonamino; sulfinamino; sulfamyl; sulfonamido; $C_{1-7}$ alkyl (including, e.g., unsubstituted $C_{1-7}$ alkyl, $C_{1-7}$ haloalkyl, $C_{1-7}$ hydroxyalkyl, $C_{1-7}$ carboxyalkyl, $C_{1-7}$ aminoalkyl, $C_{5-20}$ aryl-$C_1$-7 alkyl); $C_{3-20}$ heterocyclyl; and $C_{5-20}$ aryl (including, e.g., $C_{5-20}$ carboaryl, $C_{5-20}$ heteroaryl, $C_{1-7}$ alkyl-$C_{5-20}$ aryl and $C_{5-20}$ haloaryl) groups.

The term "ring structure" as used herein, pertains to a closed ring of from 3 to 10 covalently linked atoms, yet more preferably 3 to 8 covalently linked atoms, yet more preferably 5 to 6 covalently linked atoms. A ring may be an alicyclic ring, or aromatic ring. The term "alicyclic ring," as used herein, pertains to a ring which is not an aromatic ring.

The term "carbocyclic ring", as used herein, pertains to a ring wherein all of the ring atoms are carbon atoms.

The term "carboaromatic ring", as used herein, pertains to an aromatic ring wherein all of the ring atoms are carbon atoms.

The term "heterocyclic ring", as used herein, pertains to a ring wherein at least one of the ring atoms is a multivalent ring heteroatom, for example, nitrogen, phosphorus, silicon, oxygen or sulphur, though more commonly nitrogen, oxygen, or sulphur. Preferably, the heterocyclic ring has from 1 to 4 heteroatoms.

The above rings may be part of a "multicyclic group".

A preferred compound of the invention has formula (II):

(II)

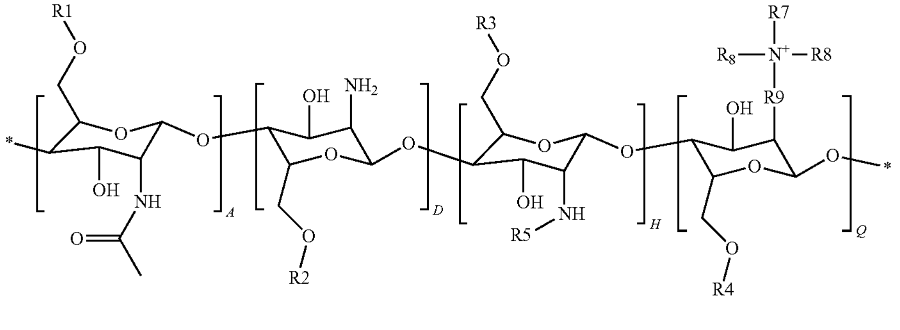

wherein:

the level of acetylated unit A is from 0.5% to 30 mole %;

the level of deacetylated unit D is from 1% to 95.5 mole %;

the level of hydrophobized unit H is from 1% to 95.5 mole %;

the level of quaternary amine unit Q is from 3% to 97.5 mole %;

and the other groups are as defined previously and the preferred percentages defined above apply.

A further preferred compound of the invention has formula (III):

lation, to quaternise an amine group and thereby form the amphiphilic carbohydrate compound.

The carbohydrate polymer may be selected from a glycol chitosan.

The carbohydrate polymer may be depolymerised with any of the following: an acid, a base, or enzyme.

The acid used to depolymerise the carbohydrate polymer may be selected from any of the following: HCl, $H_2SO$, $HNO_3$ or HF.

The carbohydrate polymer may be depolymerised for a few days, for example, 48 hours, then isolated and subjected (III)

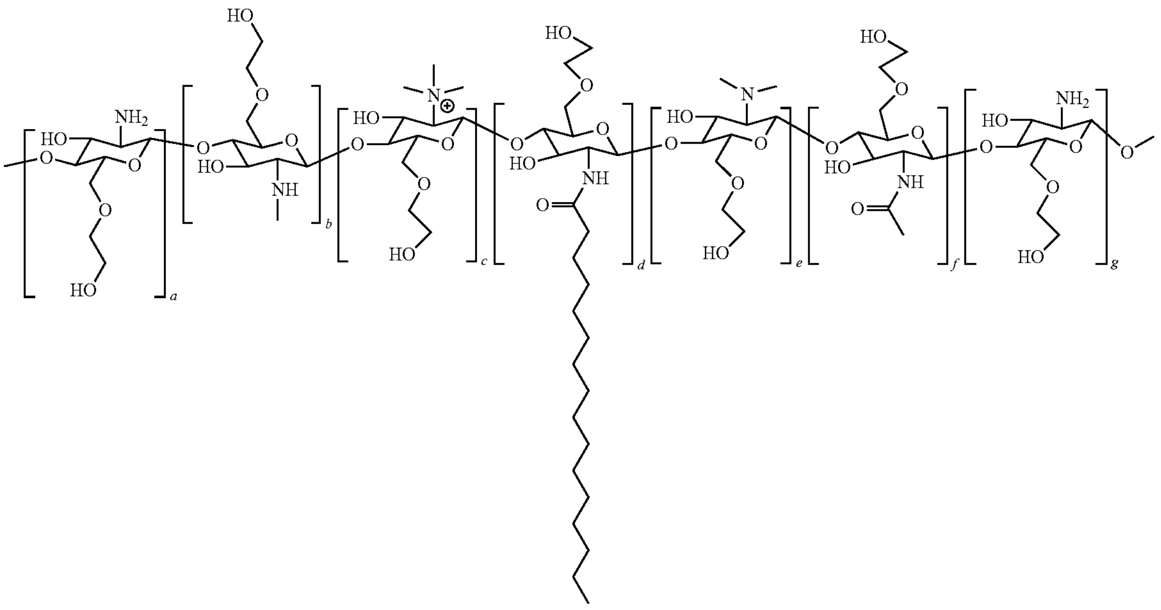

wherein:

units a and g together correspond to unit D according to claim 1;

units b and d together correspond to unit H according to claim 1;

unit c corresponds to unit Q according to claim 1;

unit e corresponds to unit T according to claim 1;

unit f corresponds to unit A according to claim 1;

the proportion of units a+b+c+d+e+f+g=1; and the corresponding levels of A, D, H, Q and T fall within the ranges defined according to claim 1;

or salt thereof.

In one embodiment of the invention there is provided a method of forming an amphiphilic carbohydrate compound of general formula (I) wherein the method comprises;

depolymerising a carbohydrate polymer to form depolymerised carbohydrate;

reacting the depolymerised carbohydrate with varying equivalents of a first reactive compound to increase, decrease or maintain the level of acetylation present;

reacting the depolymerised carbohydrate with a second reactive compound to form hydrophobic side-groups on the carbohydrate backbone and thus form hydrophobically substituted depolymerised carbohydrate; and and adding a third reactive compound to the carbohydrate compound with more, less or the same level of acetyto further depolymerisation dependent on the average molecular weight of solubilising carbohydrate polymer required.

The average molecular weight of carbohydrate polymer to be depolymerised is about 2 to 100 kD and is preferably about 5-50 kDa or 5-30 kDa.

The first reactive compound which is used in varying equivalents to increase, decrease or maintain the level of acetylation is typically acetic anhydride. Typically a degraded glycol chitosan is fully acetylated in a first reaction step and then partially deacetylated in a second reaction step to give the desired level of acetylation.

The second reactive compound which forms the hydrophobic side-groups on the depolymerised carbohydrate polymer may be selected from any of the following: any type of fatty acid derivative of, for example, stearic acid, oleic acid, palmitic acid; organo halides such as alkyl, alkenyl, alkynyl, cyclic or non-aromatic halides, acyl chlorides, anhydrides, N-hydroxysuccinimide and other activated acyl compounds capable of being attacked on the Cl carbon by a compound capable of nucleophilic attack. By nucleophilic attack is meant compounds which attack atoms with a low electron density. The acyl groups may also contain an alkyl, alkenyl or alkynyl group.

Preferably, the second reactive compound which increases, decreases or maintains the level of acetylation on the depolymerised glycol chitosan may be selected form any of the following: hexadecyl bromide, dodecyl bromide, myristic acid N-hydroxysuccinimide. Preferably, the fatty acid derivative may be palmitic acid N-hydroxysuccinimide; palmitic acid benzotriazole carbonate; palmitaldehyde; palmitoyl chloride; and palmitic acid p-nitro phenyl carbonate.

The third reactive compound may be an organo halide wherein the organo group may be selected from any linear or branch, substituted or unsubstituted, or cyclo form of any alkyl, alkenyl, alkynyl, aryl, amine, amide, alcohol or acyl group.

Typically, the third reactive compound may be any linear or branched, substituted or unsubstituted, or cyclo form of the following alkyl, alkenyl, alkynyl, aryl, amine, amide, alcohol or acyl groups: $C_1$-$C_{30}$; $C_1$-$C_{12}$; $C_1$-$C_6$; or $C_1$.

Typically, the organo group of the organo halides may be short chain linear alkyl groups.

The organo group of the organo halides may be $CH_3$.

In one aspect of the invention there is provided a pharmaceutical composition comprising an amphiphilic carbohydrate compound as discussed above, a hydrophobic drug and a pharmaceutically acceptable carrier. Pharmaceutically acceptable carriers are well known to those skilled in the art and include, but are not limited to, 0.1 M, or preferably 0.05 M phosphate buffer or 0.9% saline. Additionally, such pharmaceutically acceptable carriers may be aqueous or non-aqueous solutions, suspensions, and emulsions.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, anti-microbial, anti-oxidants, chelating agents, inert gases and the like. Typically, the ratio of carbohydrate polymer to pharmaceutical acceptable carrier ranges from 0.05 wt. % to 10 wt. %.

A hydrophobic drug is one which is poorly soluble in aqueous media, such as water. By poorly soluble drugs is meant where one gram of a drug requires more than 10,000 ml of solvent (water) to be solubilised. Alternatively, this means a drug which has a solubility of less than 0.1 $mgmL^{-1}$ in water.

The hydrophobic drug is typically encapsulated by the amphiphilic carbohydrate compound.

The hydrophobic drug may be an analgesic, antibiotic, anticoagulant, antidepressant, anticarcinogen, anticarcinoma, anti-inflammatory, antihistamine, antiemetic, anxiolytic, anticonvulsive, antipsychotic, antiviral, antidiabetic, sedative, antihypertensive or a cardiovascular drug.

The hydrophobic drug may act as a diuretic or antidiuretic, chronotrope, inotrope, decongestant, bronchodilator, anticholinergic, antithrombotic, antimicrobial or antifungal.

The hydrophobic drug is preferably a steroid. Preferred drugs include prednisolone, oestradiol, testosterone, drugs with multicyclic ring structures and lacking polar groups such as paclitaxel and drugs such as etoposide.

The hydrophobic drug is preferably a macrolide immunosuppressant drug. Macrolide drugs are of tremendous value as antimicrobial substances, particularly as antibacterial and antifungal substances, and as immunomodulatory substances. In this latter category they are particularly useful in the treatments of autoimmune disorders. Such autoimmune disorders can comprise rheumatoid arthritis, psoriasis, Crohn's disease, nephrotic syndrome, or autoimmune-derived dry eye syndrome.

Preferred macrolide drugs include rapamycin (also known as sirolimus), cyclosporine A, tacrolimus, and everolimus, and the drug is preferably cyclosporine A (CSA), rapamycin or tacrolimus. CSA is a potent immunosuppressant that has shown potential applications in ophthalmology for the treatment of corneal graft rejection and various eye disorders including keratoconjunctivitis sicca and uveitis. Due to its poor water solubility, CSA is currently formulated as an ophthalmic emulsion (Restasis®), as discussed further above. Tacrolimus (TAC) is an immune suppressant that is used to treat allergic conjunctivitis and atopic dermatitis. Rapamycin (RAP) is an immune suppressant that is for example used to prevent transplant rejection or to coat coronary stents.

Compositions of the invention can be used to treat schizophrenia, obesity, pain and sleep disorders, psychiatric diseases, neurodegenerative conditions, brain cancers or infective diseases.

The composition of the invention can be used in the treatment of ophthalmic conditions, such as dry eye syndromes (DES) (also known as keratoconjunctivitis sicca (KCS)), vernal keratoconjunctivitis (VKC), eczema, atopic keratoconjunctivitis (AKC), Sjögren syndrome, post-operative refractive surgery, corneal transplant or contact lens intolerance.

In one embodiment of the present invention, the compound cyclosporine A was solubilised at concentrations of 0.18 to 1.57 mg/mL by varying the acetylation level while maintaining other parameters of the polymer used for solubilisation.

In an embodiment of the invention, the compound tacrolimus was solubilised at concentrations of 0.07 to 1.58 mg/mL by varying the acetylation level while maintaining other parameters of the polymer used for solubilisation.

In an embodiment of the invention, the compound rapamycin was solubilised at concentrations of 0.01 to 1.34 mg/mL by varying the acetylation level while maintaining other parameters of the polymer used for solubilisation.

In the compositions of the invention the drug is preferably present at a concentration of less than 2% w/v and is preferably in the range 0.001-1% w/v.

When concentrations are expressed in % w/v, this means the amount of solid, in g, contained in 100 mL of composition.

Typically, the ratio of amphiphilic carbohydrate compound to the drug may be 10 wt. %: 5000 wt. %.

Typically, the ratio of amphiphilic carbohydrate compound to drug to pharmaceutically acceptable carrier may be about 1-20 mg: 1 mg-10 mg: 1 g.

The pharmaceutical composition may be in the form of any of the following: tablets, suppositories, liquid capsule, powder form, or a form suitable for pulmonary or nasal delivery. When tablets are used for oral administration, typically used carriers include sucrose, lactose, mannitol, maltitol, dextran, corn starch, typical lubricants such as magnesium stearate, preservatives such as paraben, sorbin, anti-oxidants such as ascorbic acid, $\alpha$-tocopheral, cysteine, disintegrators or binders. When administered orally as capsules, effective diluents include lactose and dry corn starch. A liquid for oral use includes syrup, suspension, solution and emulsion, which may contain a typical inert diluent used in this field, such as water, in addition, sweeteners or flavours may be contained. Suppositories may be prepared by admixing the compounds of the present invention with a suitable non-irritative excipient such as those that are solid at normal temperature but become liquid at the temperature in the intestine and melt in the rectum to release the active ingredient, such as cocoa butter and polyethylene glycols.

The pharmaceutical composition may be formulated for administration by any route, for instance, oral, parenteral, nasal, by inhalation or topical. It is particularly suited for topical ocular administration.

The dose can be determined on age, body weight, administration time, administration method, combination of drugs, the severity of the clinical condition or the actual condition for which a patient is undergoing therapy and other factors. While the daily doses may vary depending on the conditions and body weight of patients, the species or active ingredient, and administration route, in the case of oral use, the daily doses may be about 0.1 mg-2 g/person/day, preferably 0.5-100 mg/person/day.

In one embodiment of the invention is provided an agricultural composition comprising an amphiphilic carbohydrate compound according to the first aspect of the invention and an agrochemical agent together with agriculturally acceptable excipients.

An agriculturally acceptable carrier may be solid, liquid or both. Solid carries are essentially: mineral earth such as silicas, silica gels, silicates, talc, kaolin, montmorillonite, attapulgite, pumice, sepiolite, bentonite, limestone, lime, chalk, bole, loess, clay, dolomite, diatomaceous earth, calcite, calcium sulphate, magnesium sulphate, magnesium oxide, sand, ground plastics, fertilizers such as ammonium sulphate, ammonium phosphate, ammonium nitrate, ureas, and crushed products of vegetable origin such as cereal meal, tree bark meal, wood meal and nutshell meal, cellulose powders, or other solid carriers.

An agrochemical agent in the context of the present invention is a chemical suitable for use for agricultural purposes, and may typically be an insecticide, herbicide, fungicide or nematicide. In the present invention, the agrochemical agent is preferably a fungicide.

The invention is illustrated by the following non-limiting Examples.

EXAMPLES

Materials

Rapamycin (RAP) was purchased from Cambridge Biosciences (Cambridge, UK). Tacrolimus (TAC) was purchased from Generon Ltd. (Slough, UK). All polymers were supplied by Nanomerics Ltd.

Methods

Acetylation of dGC

Degraded glycol chitosan (dGC, MW 11.4 kDa) was dissolved in 10% v/v acetic acid to a concentration of 16.7 mg/mL and a number of molar equivalents (2, 4, 8, 10, 15, or 20) of acetic anhydride was added. The solution was shaken at room temperature for 5 hours, adjusted to pH 8-9 with powdered NaOH, dialyzed (against water, Molecular Weight Cut Off—MWCO—of dialysis bag=3.5 kDa) for 24 hours and freeze dried. The resulting product was then treated with 0.1 M KOH (30 mL/g dGC), centrifuged (8000 g, 10 min, 4° C.), washed twice with methanol (10 mL/g dGC), dissolved in water (6 mL/g dGC), and freeze dried.

Deacetylation of dGC

Degraded glycol chitosan (dGC, MW 11.4 kDa) was added to a boiling solution of 45% w/v NaOH, the reaction proceeded under nitrogen for 1 hour, after which the pH was adjusted to 7 with HCl. The solution was then dialyzed ($H_2O$, MWCO=3.5 kDa, 24 hours) and freeze dried.

Palmitoylation of dGC

Palmitoylation was carried out as previously described with minor changes. Briefly, dGC was dissolved in 3.7% v/v triethylamine/DMSO to a concentration of 30 mg/mL, to this solution was added 0.25 molar equivalents palmitic acid N-hydroxysuccinimide, relative to the molar concentration of free amines (degree of deacetylation as determined by NMR), the reaction proceeded protected from light for 16 hours. The product was precipitated and washed with acetone.

Quaternization of pGC

Quaternization was carried out as previously described. Briefly, pGC, NaOH, and NaI were dissolved in NMP to concentrations of 15.1, 16.3, and 18.6 mg/mL respectively. The solutions were combined in order at a ratio of 7:2:1, purging with nitrogen for 15 minutes after addition of NaI solution. MeI was added (1.5 mL/g pGC) and the reaction proceeded with magnetic stirring for 2 hours at 37° C. under a nitrogen atmosphere. GCPQ was precipitated by addition to 6 vols methyl tert-butyl. ether (MTBE), washed 3 times with 1 vol MTBE, dialyzed ($H_2O$, MWCO=3.5 kDa, 24 hours), ion exchanged against IRA-410, and finally freeze dried. The resulting N-palmitoyl-N-acetyl-N-monomethyl-N, N-dimethyl-N, N, N-trimethyl-6-O-glycolchitosan (AGCPQ) was recovered as a freeze-dried powder.

Determination of Polymer Levels of Modification DA (degree of acetylation) was determined by 1H NMR by comparing the integration of the acetyl peak at 2.02-2.10 ppm (1.5 protons per half acetyl group) to the sugar/glycol peaks at 3.44-4.40 ppm (nominally 9 protons per GC unit). Similarly, palmitoylation (DP) and quaternization (DQ) were determined by comparing peaks at 0.85-1.00 ppm (3 protons per terminal methyl) and 0.35-3.43 ppm (4.5 protons per half quaternary amine). These ranges are representative and are better defined by the relevant peaks and troughs (FIG. 1).

Cyclosporine A (CsA) Encapsulation

GCPQ (7.5 mg) was dispersed in glycerol (3.1% w/v, 1 mL) with shaking for >2 hours. This dispersion was then used to rehydrate 2 mg cyclosporine which had previously been dissolved in methanol, aliquoted, and dried under nitrogen. The resulting solution was shaken for >2 hours, sonicated at amplitude 5 for 3 minutes, and refrigerated overnight. The supernatant was then collected, and the cyclosporine concentration determined by HPLC.

Tacrolimus Encapsulation

TAC powder was dissolved in absolute ethanol (2 mg/mL, 1.5 mL). Polymers were dispersed in a 50:50% v/v Ethanol: Methanol mixture (10 mg/mL, 1 mL). Both preparations were mixed, and 0.4 mL of methanol added to each mixture to ensure full dissolution of all components. The organic solvent was then removed under vacuum until a thin, dry film was formed. The dry film was rehydrated with 1.5 mL of distilled water and mixed vigorously for 30 min to disperse the film in the solvent. The formulations were adjusted to a pH of 4.0-5.0 in a calibrated pH meter using 1.0 M NaOH, and then submitted to a simulated sterile filtration step using a 0.22 μm PES sterile filter. All formulations were then analysed for drug content using RP-HPLC (parameters in Table 1).

TABLE 1

| HPLC-UV-Vis parameters for tacrolimus quantification | | |
|---|---|---|
| Parameter | Value | |
| Mobile Phase | A: 0.1% H3PO4 in H2O | |
| | B: Acetonitrile | |
| Flow rate | 1.0 mL/min | |
| Gradient | Time (min) | % B |
| | 0 | 60 |
| | 4 | 95 |
| | 5.5 | 95 |
| | 7.0 | 60 |
| Post time | Off | |
| Injection | 10 μL | |
| Column | Onyx Monolithic | |
| Parameter | Value | |
| | 100 × 4.6 mm | |
| | CH0-7643 | |
| Column temp | 50° C. | |
| Detector wavelength | 215 nm | |

Rapamycin Encapsulation

RAP powder was dissolved in absolute ethanol (5 mg/mL, 0.4 mL). Polymers were dispersed in a 50:50% v/v water: Methanol mixture (7.5 mg/mL, 0.5 mL). Both preparations were mixed, and 0.4 mL of methanol added to each mixture to ensure full dissolution of all components. All preparations were mixed and placed in a Savant Vacuum Evaporator at 45° C. and spun under vacuum for 5 h until a thin, dry film was formed. The dry film was rehydrated with 1 mL of distilled water and mixed vigorously for 30 min to disperse the film in the solvent. The mixture was subsequently sonicated using MSE Soniprep 150 sonicator at 30% of its maximum output for 3 minutes in an ice bath. The formulations were adjusted to a pH of 4.0-5.0 in a calibrated PH meter using 1.0 M NaOH, and then submitted to a simulated sterile filtration step using a 0.22 μm PES sterile filter. All formulations were then analysed for drug content using RP-HPLC (parameters in Table 2).

TABLE 2

| HPLC-UV-Vis parameters for rapamycin quantification | | |
|---|---|---|
| Parameter | Value | |
| Mobile Phase | A: 0.1% H3PO4 in H2O | |
| | B: Acetonitrile | |
| Flow rate | 1.0 mL/min | |
| Gradient | Time (min) | % B |
| | 0 | 30 |
| | 3 | 90 |
| | 4 | 90 |
| | 8 | 90 |
| | 9 | 30 |
| Post time | Off | |
| Injection | 10 μL | |
| Column | Onyx Monolithic | |
| | 100 × 4.6 mm | |
| | CHO-7643 | |
| Column temp | 50° C. | |
| Detector wavelength | 298 nm | |

Results and Discussion

Acetylation of dGC

Levels of acetylation were able to be tightly controlled in the range tested—2-20 molar equivalents of acetic anhydride ($Ac_2O$)—providing degrees of acetylation (DAs) of 5.5-16.4%, resulting in a linear correlation of $DA=0.0059*AC_2O+0.0449$ $R^2=0.9976$, highlighting the precision with which the DA can be controlled (Table 3).

TABLE 3

| Equivalents of $AC_2O$ and resulting DA for each tested equivalent | | | | | | |
|---|---|---|---|---|---|---|
| Equiv. $Ac_2O$ | 2 | 4 | 8 | 10 | 15 | 20 |
| DA | 5.5% | 6.8% | 9.6% | 10.5% | 13.2% | 16.4% |

Cyclosporine (CsA) Encapsulation

The target DP and DQ was the same for every AGCPQ polymer, however these parameters varied as the degree of acetylation varied (Table 4). The concentration of CsA [CsA] was plotted against the DA, DP, and DQ of the polymer being tested and showed a negative correlation with DA and no significant correlation with other properties of the polymer (Table 5), therefore the DA is shown to have a significant impact on encapsulation.

TABLE 4

| Properties of tested polymers and their CsA encapsulation levels. | | | | |
|---|---|---|---|---|
| Polymers | DA % | DP % | DQ % | [CsA] mg/mL |
| (daGC)PQ | 2.85 | 21.23 | 6.12 | 1.57 |
| RM GCPQ 1 | 4.58 | 21.94 | 9.92 | 1.23 |
| (aGC)PQ0 | 10.56 | 18.84 | 9.56 | 1.11 |
| (aGC)PQ10 | 26.4 | 14.14 | 7.84 | 0.88 |
| (aGC)PQ20 | 37.55 | 24.2 | 13.99 | 0.18 |

TABLE 5

| Effect of CsA encapsulation on the DA, DP and | | |
|---|---|---|
| Molecular Parameter | Linear equation | Square of the correlation coefficient |
| Degree of acetylation (DA) | DA = −3.28 [CsA] + 1.53 | 0.9013 |
| Degree of palmitoylation (DP) | DP = −2.94 [CsA] + 1.58 | 0.0469 |
| Degree of quarternisation (DQ) | DQ = −15.37 [CsA] + 2.45 | 0.7577 |

Mathematical Model

While DA is having the most pronounced impact on encapsulation, DP and DQ were incorporated into a model to refine its predictive power. Using the sum of products for each polymer variable and a coefficient as well as a constant, each polymer provided a predicted [CsA], coefficients were varied to minimize the error between predicted and observed values. Coefficients for DA, DP, and DQ were −2.21, 0.44, and −8.07 respectively, $R^2$ for the model was 1, suggesting that [CsA] increases with increasing DP and decreasing DA and DQ.

$$[CSA]=(-2.21*DA)+(0.44*DP)+(-8.07*DQ)+2.03 \quad \text{(Eqn. 1)}$$

Tacrolimus (TAC) Encapsulation

The concentration of tacrolimus [TAC] was plotted against the DA, DP, and DQ of the polymer being tested (Table 6).

TABLE 6

Properties of polymers tested and resulting tacrolimus encapsulation

| Polymers | DA (mole %) | DP (mole %) | DQ (mole %) | [TAC] (mg/mL) |
|---|---|---|---|---|
| (daGC)PQ | 4.3 | 21.6 | 11.0 | 1.58 |
| GCPQ | 5.4 | 22.6 | 13.2 | 1.37 |
| (aGC)PQ0 | 14.6 | 16.4 | 12.8 | 0.37 |
| (aGC)PQ10 | 27.2 | 15.5 | 13.0 | 0.49 |
| (aGC)PQ20 | 40.5 | 18.8 | 13.2 | 0.07 |

Rapamycin (RAP) Encapsulation

The concentration of rapamycin [RAP] was plotted against the DA, DP, and DQ of the polymer being tested (Table 7).

TABLE 7

Properties of polymers tested and resulting rapamycin encapsulation

| Polymers | DA (mole %) | DP (mole %) | DQ (mole %) | [RAP] (mg/mL) |
|---|---|---|---|---|
| (daGC)PQ | 4.3 | 21.6 | 11.0 | 1.34 |
| GCPQ | 5.4 | 22.6 | 13.2 | 0.45 |
| (aGC)PQ0 | 14.6 | 16.4 | 12.8 | 0.21 |
| (aGC)PQ10 | 27.2 | 15.5 | 13.0 | 0.23 |
| (aGC)PQ20 | 40.5 | 18.8 | 13.2 | 0.01 |

CONCLUSIONS

The hypothesis for this study was that increasing the degree of acetylation of GCPQ would allow for stronger hydrophobic interaction with hydrophobic molecules and therefore increased encapsulation, however the opposite was observed.

We unexpectedly found that a level of acetylation of between 2 and 27% in N-palmitoyl, N-monomethyl, N, N-dimethyl, N, N, N-trimethyl-6-O-glycolchitosan, was able to produce the best molecules to encapsulate hydrophobic compounds and that increasing levels of acetylation to 37.6% led to a significant reduction in drug encapsulation.

While the DP and DQ also varied in the polymers tested, these parameters can reliably be ruled out as a dominant explanation for the observed results as there was no apparent trend between either property with encapsulation. The only clear trend was the negative correlation between DA and encapsulation, one explanation for this is that acetyl groups on the polymer have little contribution to hydrophobic interaction but serve to sterically hinder the folding of the polymer, necessary for efficient encapsulation of a small hydrophobic compound.

Previous work has shown that DP and DQ effect encapsulation of hydrophobic compounds in the polymer nano-assemblies. This is the first time that DA has been systematically varied and studied for its effect on hydrophobic compound encapsulation. Controlling DA is shown to be an effective means of increasing the encapsulation of hydrophobic compounds. Increased encapsulation of hydrophobic compounds means that higher levels of compound may be loaded on to these nano-assemblies, making drug delivery more efficient.

The same conclusion is seen with tacrolimus and rapamycin, in that the level of drug encapsulated in polymer nanoparticles increases with a decrease in the level of polymer acetylation.

What is claimed is:

1. An amphiphilic carbohydrate compound of average molecular weight 1-50 kDa of formula (I):

(I)

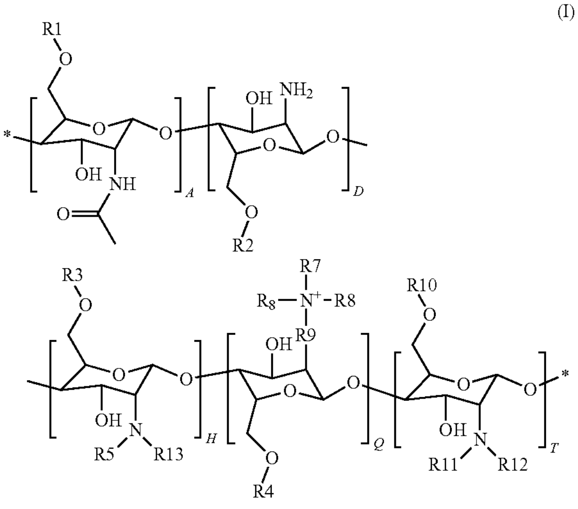

wherein:

the level of unit A is from 2% to 27 mole %;

the level of unit D is from 1% to 95.5 mole %;

the level of unit H is from 1% to 95.5 mole %;

the level of unit Q is from 1% to 90 mole %;

the level of unit T is from 0% to 94.5 mole %;

$R^1$, $R^2$, $R^3$, $R^4$ and $R^{10}$ are independently hydrogen or any linear, branched or cyclo form of an alkyl, alkenyl, alkynyl, aryl, acyl group or polyoxyalkylene with $C_1$-$C_3$ alkylene units, optionally substituted with amine, amide or alcohol;

$R^5$ is a hydrophobic, substituted or unsubstituted, linear, branched or cyclo form of a $C_{4-30}$ alkyl, $C_{4-30}$ alkenyl, $C_{4-30}$ alkynyl, $C_{4-30}$ aryl, amine, $C_{4-30}$ amide, $C_{4-30}$ alcohol or $C_{3-30}$ acyl group;

$R^6$, $R^7$, and $R^8$ are independently any linear, branched, or cyclo forms of any alkyl, alkenyl, alkynyl, aryl or acyl group;

$R^9$ is present or absent and, when present, is a substituted or unsubstituted alkyl group, a substituted or unsubstituted amine group or a substituted or unsubstituted amide group;

$R^{11}$ is a substituted or unsubstituted alkyl group, a substituted or unsubstituted ether group or a substituted or unsubstituted alkene group or hydrogen; and $R^{12}$ is a substituted or unsubstituted alkyl group, a substituted or unsubstituted ether group or a substituted or unsubstituted alkene group;

$R^{13}$ is a substituted or unsubstituted alkyl group, a substituted or unsubstituted ether group or a substituted or unsubstituted alkene group or hydrogen;

or a salt thereof;

wherein the A, D, H and Q units form a linkage of any arrangement and * is used to represent the continuing polymer chain.

2. The amphiphilic carbohydrate compound according to claim 1, wherein the compound has the formula:

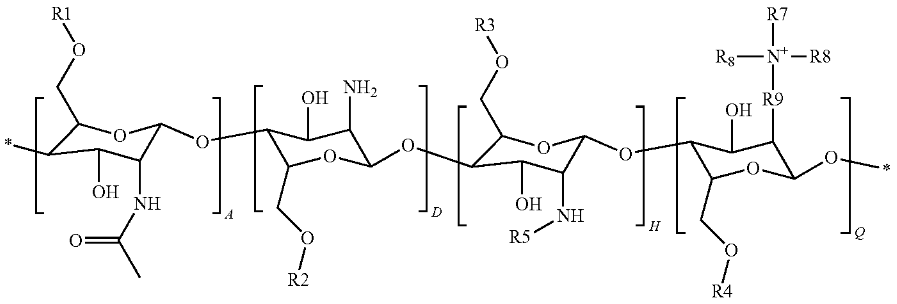

wherein:

the level of acetylated unit A is from 2% to 27 mole %;

the level of deacetylated unit D is from 1% to 95.5 mole %;

the level of hydrophobized unit H is from 1% to 95.5 mole %;

the level of quaternary amine unit Q is from 1% to 90 mole %;

$R^1$, $R^2$, $R^3$, and $R^4$ are independently any linear, branched or cyclo form of an alkyl, alkenyl, alkynyl, aryl, acyl group, or polyoxyalkylene with $C_1$-$C_3$ alkylene units, optionally substituted with amine, amide or alcohol;

$R^5$ is a hydrophobic, substituted or unsubstituted, linear, branched or cyclo form of a $C_{4-30}$ alkyl, $C_{4-30}$ alkenyl, $C_{4-30}$ alkynyl, $C_{4-30}$ aryl, amine, $C_{4-30}$ amide, $C_{4-30}$ alcohol or $C_{3-30}$ acyl group; and $R^6$, $R^7$, and $R^8$ are independently any linear, branched, or cyclo forms of any alkyl, alkenyl, alkynyl, aryl or acyl group;

or a salt thereof.

3. The amphiphilic carbohydrate compound according to claim 1, wherein the compound has the formula:

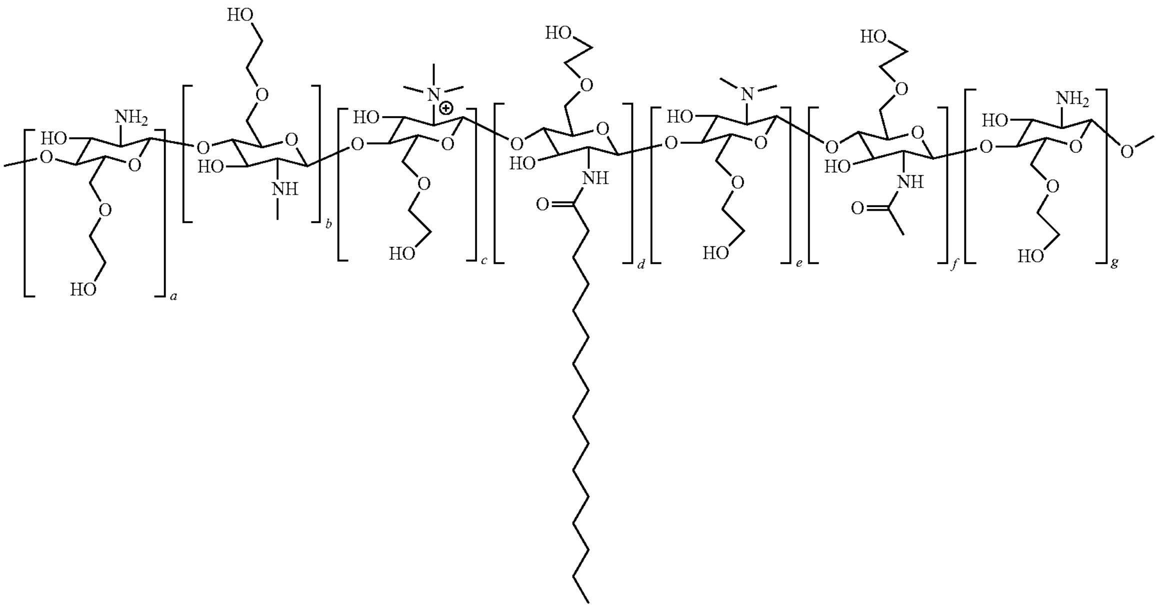

or salt thereof, wherein:

the level of units a plus g is from 1% to 95.5 mole %;

the level of units b plus d is from 1% to 95.5 mole %;

the level of unit c is from 1% to 90 mole %;

the level of unit e is from 0% to 94.5 mole %;

the level of unit f is from 2% to 27 mole %; and the proportion of units a+b+c+d+e+f+g=100 mole %.

4. The amphiphilic carbohydrate compound according to claim 1, wherein the A, D, H, Q and T units, if present, form any arrangement in the linkage.

5. The amphiphilic carbohydrate compound according to claim 1, wherein the level of acetylated unit A is in the range 2-26 mole % or 2-20 mole %.

6. The amphiphilic carbohydrate compound according to claim 1, wherein the level of hydrophobized unit H is in the range 2-94.5 mole %.

7. The amphiphilic carbohydrate compound according to claim 1, wherein the level of quaternary amine unit Q is in the range 5-30 mole %.

8. The amphiphilic carbohydrate compound according to claim 1, wherein A is in the range 2 to 27 mole %; H is in the range 14 to 24 mole %; and Q is in the range 6 to 14 mole %.

9. The amphiphilic carbohydrate compound according to claim 1, wherein the compound is a partially acetylated form of N-palmitoyl, N-monomethyl, N,N-dimethyl,N,N,N-trimethyl-6-O-glycolchitosan (GCPQ).

10. A pharmaceutical composition comprising an amphiphilic carbohydrate compound according to claim 1, a hydrophobic drug, and one or more pharmaceutically acceptable excipients.

11. The pharmaceutical composition according to claim 10, wherein the hydrophobic drug is an analgesic, antibiotic, anticoagulant, antidepressant, anticarcinogen, anticarcinoma, anti-inflammatory, antihistamine, antiemetic, anxiolytic, anticonvulsive, antipsychotic, antiviral, antidiabetic, sedative, antihypertensive, or cardiovascular drug.

12. The pharmaceutical composition according to claim 11, wherein the hydrophobic drug is a macrolide immunosuppressant drug.

13. The pharmaceutical composition according to claim 10, wherein the concentration of the hydrophobic drug is from 0.01% to 0.2% w/v.

14. The composition according to claim 12, wherein the immunosuppressant drug is cyclosporine A, tacrolimus, or rapamycin.

15. A method of treating an autoimmune disorder, comprising administering to a human or animal subject in need thereof a pharmaceutical composition according to claim 12.

16. The method according to claim 15, wherein the composition is administered topically to the ocular region of the subject.

17. The method according to claim 15, wherein the composition is administered orally to the subject.

18. The method according to claim 15, wherein the autoimmune disorders is rheumatoid arthritis, psoriasis, Crohn's disease, nephrotic syndrome, dry eye syndromes (DES) (also known as keratoconjunctivitis sicca (KCS)), vernal keratoconjunctivitis (VKC), eczema, atopic keratoconjunctivitis (AKC), Sjögren syndrome, post-operative refractive surgery, corneal transplant or contact lens intolerance.

19. A method of forming the amphiphilic carbohydrate compound according to claim 1, the method comprising:

a step for depolymerisation of a carbohydrate compound;

a step for increasing, decreasing or maintaining the level of acetylation in the carbohydrate compound;

a step for reacting the acetylated carbohydrate compound with a first compound to add a hydrophobic side chain; and a step for reacting with a second compound to quaternize an amine of the acetylated carbohydrate with added hydrophobic side chain compound to obtain the amphiphilic carbohydrate of claim 1.

* * * * *